US011084873B2

(12) United States Patent
Shie et al.

(10) Patent No.: US 11,084,873 B2
(45) Date of Patent: Aug. 10, 2021

(54) ANTI-ABETA ANTIBODIES AND USES THEREOF

(71) Applicant: National Health Research Institutes, Miaoli County (TW)

(72) Inventors: Feng-Shiun Shie, Miaoli County (TW); Tsu-An Hsu, Miaoli County (TW); Chuan Shih, Carmel, IN (US); Santai Shen, Miaoli County (TW)

(73) Assignee: National Health Research Institutes, Miaoli County (TW)

(*) Notice: Subject to any disclaimer, the term of this patent is extended or adjusted under 35 U.S.C. 154(b) by 3 days.

(21) Appl. No.: 16/426,585

(22) Filed: May 30, 2019

(65) Prior Publication Data

US 2019/0367593 A1 Dec. 5, 2019

Related U.S. Application Data

(60) Provisional application No. 62/678,080, filed on May 30, 2018.

(51) Int. Cl.
| | |
|---|---|
| *C07K 16/18* | (2006.01) |
| *A61P 25/28* | (2006.01) |
| *G01N 33/68* | (2006.01) |
| *G01N 33/60* | (2006.01) |
| *A61K 39/00* | (2006.01) |

(52) U.S. Cl.
CPC .............. *C07K 16/18* (2013.01); *A61P 25/28* (2018.01); *G01N 33/60* (2013.01); *G01N 33/6896* (2013.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
CPC ............... C07K 16/18; C07K 2317/24; C07K 2317/76; C07K 2317/92; C07K 2317/565; A61P 25/28; A61K 2039/505
See application file for complete search history.

(56) References Cited

U.S. PATENT DOCUMENTS

| | | | |
|---|---|---|---|
| 2009/0142270 | A1 | 6/2009 | Schroeter et al. |
| 2011/0176995 | A1 | 7/2011 | Funahashi |
| 2012/0177664 | A1 | 7/2012 | Yokoseki et al. |
| 2012/0288896 | A1 | 11/2012 | Greferath et al. |
| 2015/0315267 | A1 | 11/2015 | Bussiere et al. |

FOREIGN PATENT DOCUMENTS

| | | | |
|---|---|---|---|
| WO | WO-2009033743 A1 * | 3/2009 | ............ C07K 16/18 |
| WO | WO-2015/161311 | 10/2015 | |

OTHER PUBLICATIONS

Paul W. E. Fundamental Immunology, 3rd edition, 1993, pp. 292-295.*
Rudikoff et al. Single amino acid substitution altering antigen-binding specificity. Proc Natl Acad Sci U S A. Mar. 1982;79(6):1979-83.*
Rasmussen et al "Hypothetical Protein UA08_03765 [Talaromyces Atroroseus]" National Center for Biotechnology Information Reference Sequence XP_020121409.1.
Barrera-Ocampo et al "Amyloid-Beta Immunotherapy: The Hope for Alzheimer Disease?" Colombia Medica vol. 47, pp. 203-212, 2016.
Wang et al "A Systemic View of Alzheimer Disease—Insights From Amyloid-β Metabolism Beyond the Brain" Nature Reviews vol. 13, pp. 612-623, 2017.

* cited by examiner

*Primary Examiner* — Gregory S Emch
(74) *Attorney, Agent, or Firm* — Cesari & McKenna, LLP

(57) ABSTRACT

An isolated antibody, comprising a light-chain CDR1 (L-CDR1) having the sequence of SEQ ID NO: 1, SEQ ID NO: 7, or SEQ ID NO: 14; a light-chain CDR2 (L-CDR2) having the sequence of SEQ ID NO: 2 or SEQ ID NO: 15; a light-chain CDR3 (L-CDR3) having the sequence of SEQ ID NO: 3, SEQ ID NO: 8, SEQ ID NO: 21, or SEQ ID NO: 24; a heavy-chain CDR1 (H-CDR1) having the sequence of SEQ ID NO: 4, SEQ ID NO: 9, SEQ ID NO: 11, SEQ ID NO: 16, or SEQ ID NO: 25; a heavy-chain CDR2 (H-CDR2) having the sequence of SEQ ID NO: 5, SEQ ID NO: 12, SEQ ID NO: 17, SEQ ID NO: 19, SEQ ID NO: 22, or SEQ ID NO: 26; and a heavy-chain CDR3 (H-CDR3) having the sequence of SEQ ID NO: 6, SEQ ID NO: 10, SEQ ID NO: 13, SEQ ID NO: 18, SEQ ID NO: 20, SEQ ID NO: 23, or SEQ ID NO: 27, wherein the antibody specifically binds to $A\beta_{1-42}$ or an N-terminal modified form thereof.

20 Claims, 13 Drawing Sheets

Specification includes a Sequence Listing.

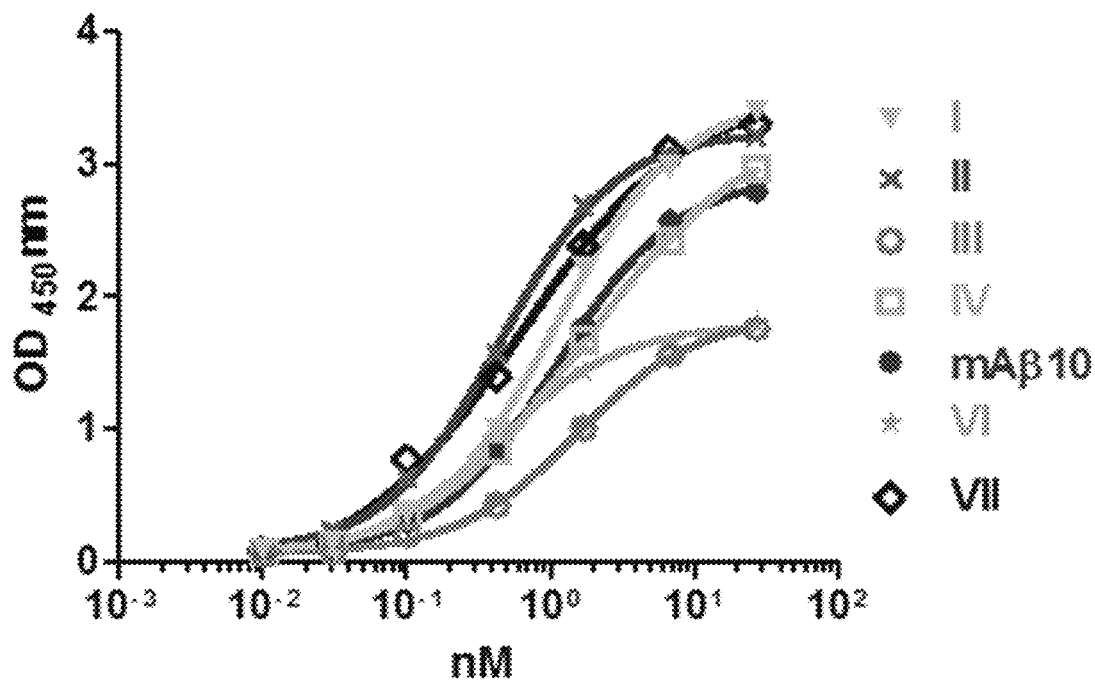

B.

| | Aβ$_{1-42}$ | DAEFRHDSGYEVHHQKLVFFAEDVGSNKGAIIGLMVGGVVIA (SEQ ID NO: 28) |
|---|---|---|
| SEQ ID NO: 29 | 1. | biotin- DAEFRHDSGYGSG |
| SEQ ID NO: 30 | 2. | biotin- SGSGEFRHDSGYEV |
| SEQ ID NO: 31 | 3. | biotin- SGSGRHDSGYEVHH |
| SEQ ID NO: 32 | 4. | biotin- SGSGDSGYEVHHQK |
| SEQ ID NO: 33 | 5. | biotin- SGSGGYEVHHQKLV |
| SEQ ID NO: 34 | 6. | biotin- SGSGEVHHQKLVFF |
| SEQ ID NO: 35 | 7. | biotin- SGSGHHQKLVFFAE |
| SEQ ID NO: 36 | 8. | biotin- SGSG QKLVFFAEDV |
| SEQ ID NO: 37 | 9. | biotin- SGSG LVFFAEDVGS |
| SEQ ID NO: 38 | 10. | biotin- SGSG FFAEDVGSNK |
| SEQ ID NO: 39 | 11. | biotin- SGSG AEDVGSNKGA |
| SEQ ID NO: 40 | 12. | biotin- SGSG DVGSNKGAIIG |
| SEQ ID NO: 41 | 13. | biotin- SGSG GSNKGAIIGLM |
| SEQ ID NO: 42 | 14. | biotin- SGSG NKGAIIGLMVG |
| SEQ ID NO: 43 | 15. | biotin- SGSG GAIIGLMVGGV |
| SEQ ID NO: 44 | 16 | biotin- SGSG IIGLMVGGVV |
| SEQ ID NO: 45 | 17. | biotin- SGSGGLMVGGVVIA |

| Antibodies /isotype | CDR-L1 | CDR-L2 | CDR-L3 | CDR-H1 | CDR-H2 | CDR-H3 |
|---|---|---|---|---|---|---|
| I/IgG2a | SEQ ID NO: 1<br>CRSSQTIVHSNGNTYLE | SEQ ID NO: 2<br>KVSNRFS | SEQ ID NO: 3<br>FQGSHVPLT | SEQ ID NO: 4<br>TSGMNVG | SEQ ID NO: 5<br>HIWWDDDKYYNPSLKS | SEQ ID NO: 6<br>RRSIR--GSDYFDY |
| II/IgG1 | SEQ ID NO: 7<br>CRSSQSIVHSNGNTYLE | KVSNRFS | SEQ ID NO: 8<br>FQGSLVPLT | SEQ ID NO: 9<br>TSGMGVG | HIWDDDKYYNPSLKS | SEQ ID NO: 10<br>RRALRNVVADAMDY |
| III/IgG3 | CRSSQSIVHSNGNTYLE | KVSNRFS | FQGSHVPLT | SEQ ID NO: 11<br>TSAVGVS | SEQ ID NO: 12<br>HIYWDDDKRYNPSLKS | SEQ ID NO: 13<br>RRPYYRYDVDAMDY |
| IV/IgG2b | SEQ ID NO: 14<br>CRSSQNIVHSNGNTYLE | SEQ ID NO: 15<br>TVSNRFS | FQGSHVPLT | SEQ ID NO: 16<br>SSVLGVS | SEQ ID NO: 17<br>HIYWDDDRRYNPSLKS | SEQ ID NO: 18<br>RRGKMGRGLDAMDY |
| V (mAβ-10)/IgG2a | CRSSQNIVHSNGNTYLE | TVSNRFS | FQGSHVPLT | SSVLGVS | SEQ ID NO: 19<br>HIYWDDDRRYNPSLRS | SEQ ID NO: 20<br>RRGKMGRGLDALDF |
| VI/IgG2b | CRSSQSIVHSNGNTYLE | KVSNRFS | SEQ ID NO: 21<br>FQGSRVPLT | TSGMGVG | SEQ ID NO: 22<br>HIWWDDDKYFNPSLKS | SEQ ID NO: 23<br>RRSLK--WLDAMDY |
| VII/IgG1 | CRSSQSIVHSNGNTYLE | KVSNRFS | SEQ ID NO: 24<br>FQSSRVPLT | SEQ ID NO: 25<br>TSGMGVS | SEQ ID NO: 26<br>HIYWDDDKSYNPSLKS | SEQ ID NO: 27<br>RRRNW--VITDAMEY |

Fig. 2
A.
| | ka(1/Ms) | Kd (1/s) | KD (nM) |
|---|---|---|---|
| I | 1.7E+04 | 3.0E-04 | 17.25 |
| II | 6.3E+04 | 6.8E-04 | 10.87 |
| III | 9.8E+04 | 2.5E-04 | 2.56 |
| IV | 1.3E+05 | 4.9E-04 | 3.84 |
| chAβ10 | 5.3E+04 | 2.1E-04 | 3.91 |
| VI | 5.4E+04 | 1.4E-04 | 2.63 |
| VII | 1.5E+05 | 8.4E-05 | 0.55 |
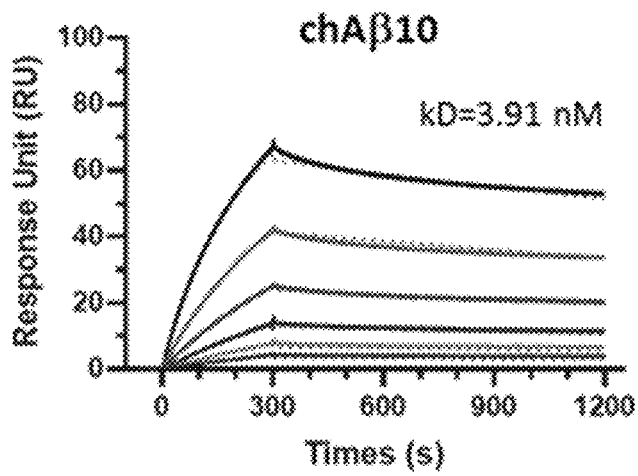
B.
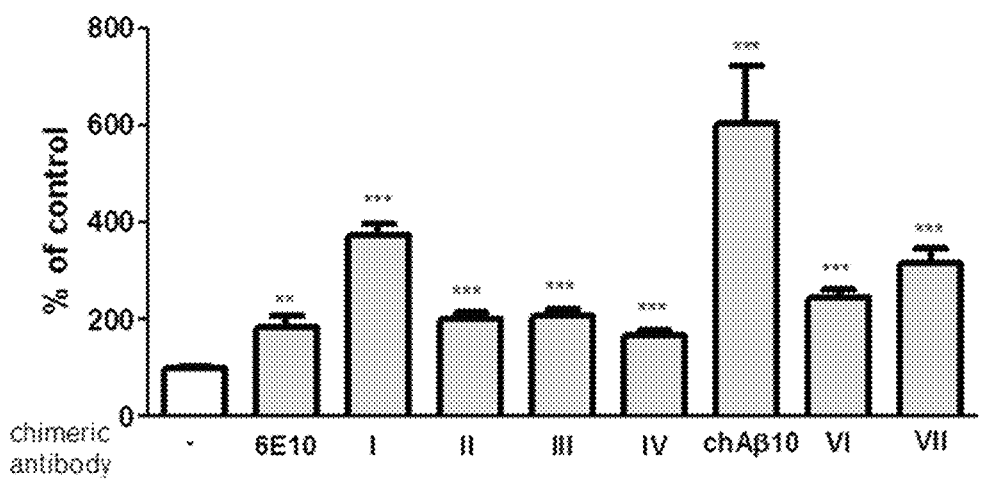

Fig. 3
A.
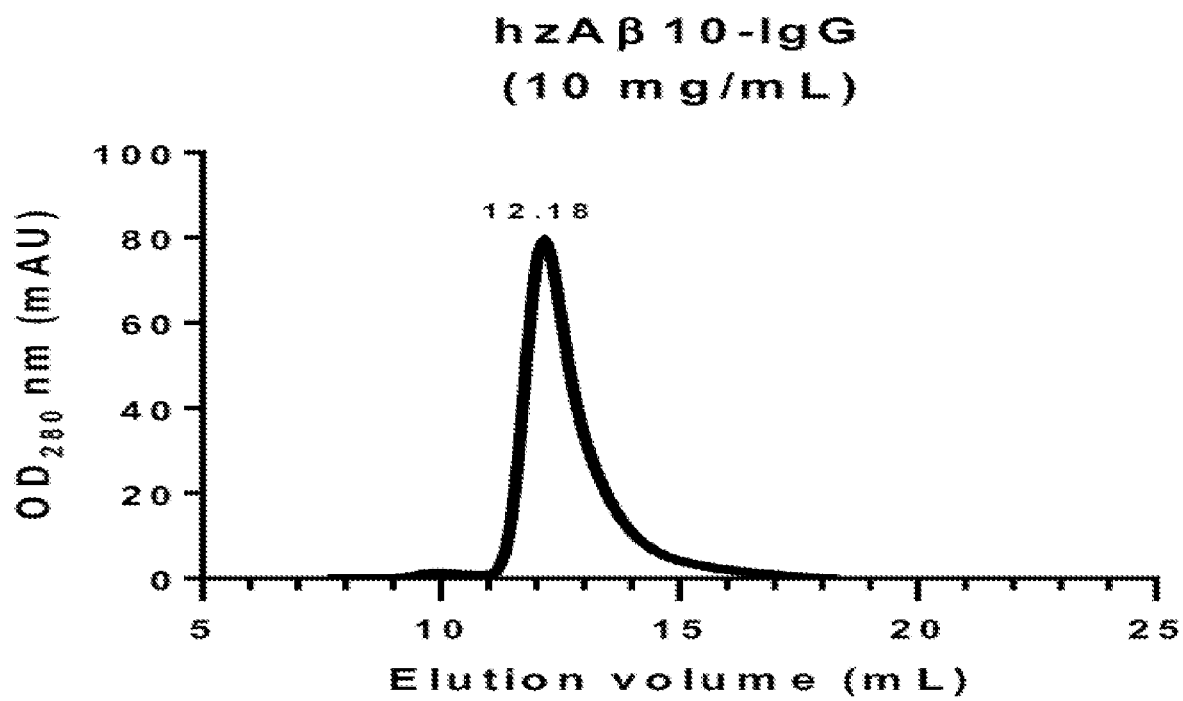
B.
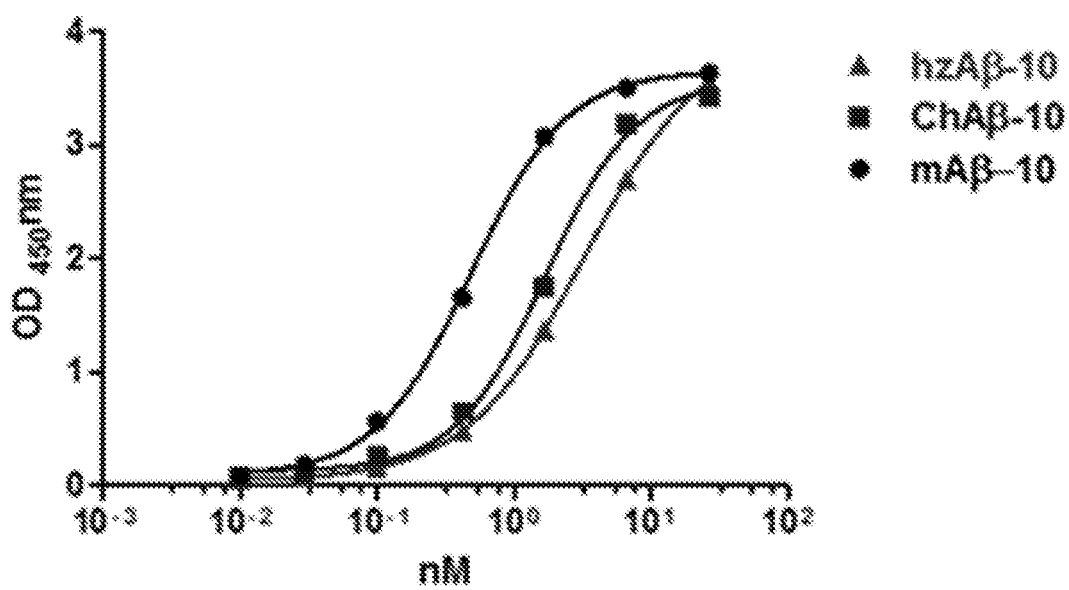

C.

A.

B.

|  |  | Ka | kd | KD (nM) |
|---|---|---|---|---|
| pE-Aβ₃₋₄₂ | mAβ-10 | 3.7E+04 | 5.2E-04 | 14.22 |
|  | chAβ-10 | 2.5E+04 | 8.3E-04 | 32.59 |
|  | hzAβ-10 | 1.7E+04 | 7.6E-04 | 44.70 |
| Aβ₁₋₄₂ | mAβ-10 | 8.7E+04 | 1.1E-04 | 1.29 |
|  | chAβ-10 | 5.3E+04 | 2.1E-04 | 3.91 |
|  | hzAβ-10 | 4.0E+04 | 1.6E-04 | 3.96 |

C.

FIG. 5
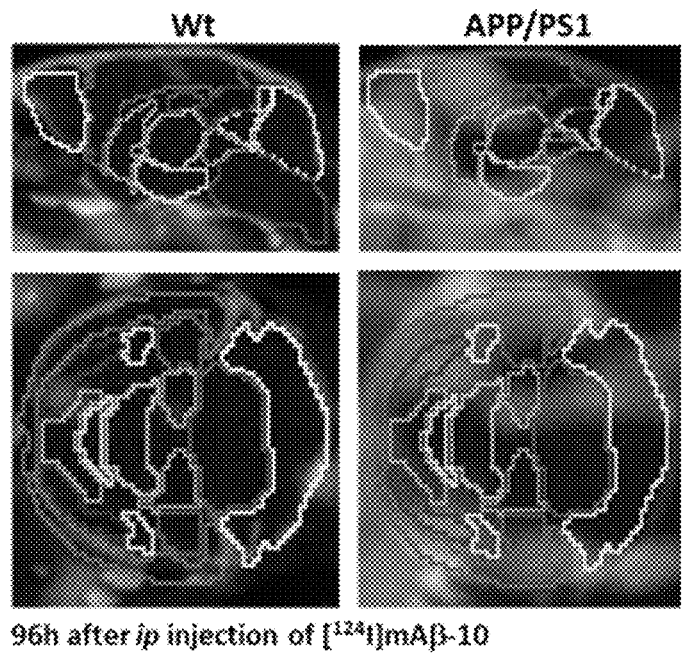
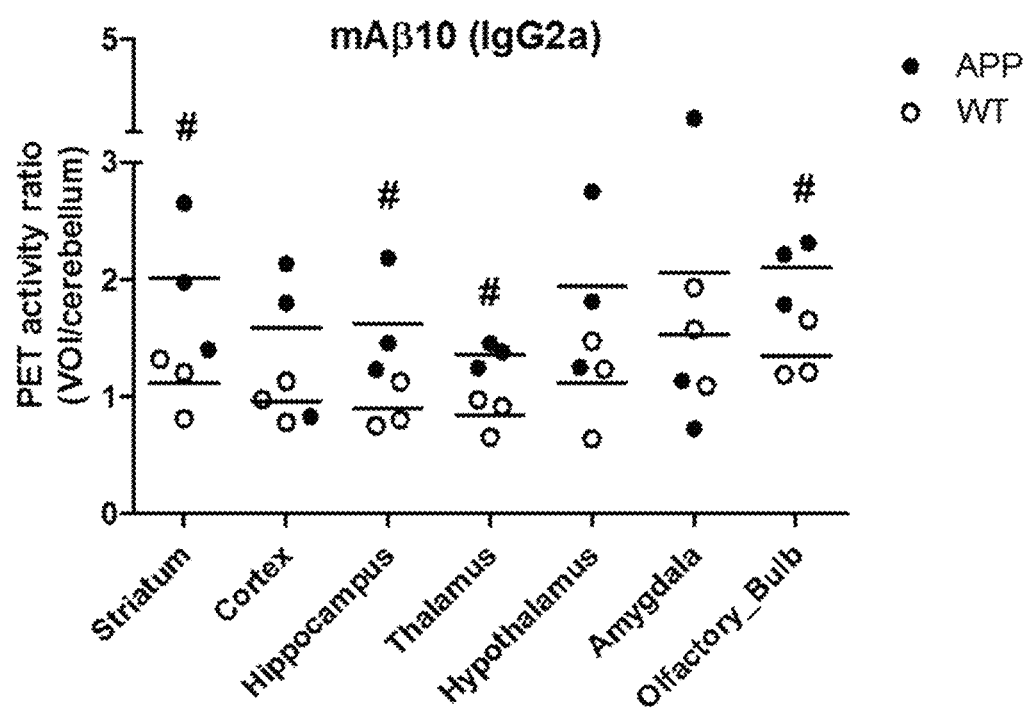

FIG. 8
A.
| CDR-H (average%) | CDR-H1 | CDR-H2 | CDR-H3 | CDR-L (average%) | CDR-L1 | CDR-L2 | CDR-L3 |
|---|---|---|---|---|---|---|---|
| 27.4 | 28.6 | 25.0 | 28.6 | 34.8 | 31.3 | 28.6 | 44.4 |
B.
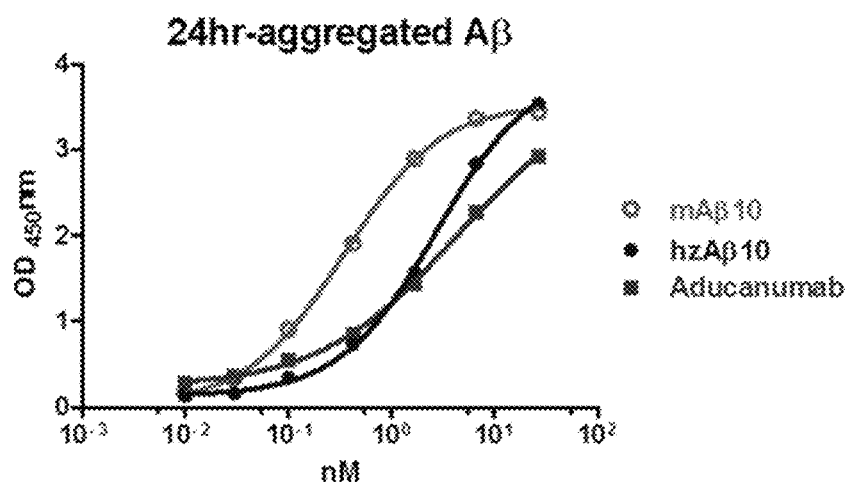
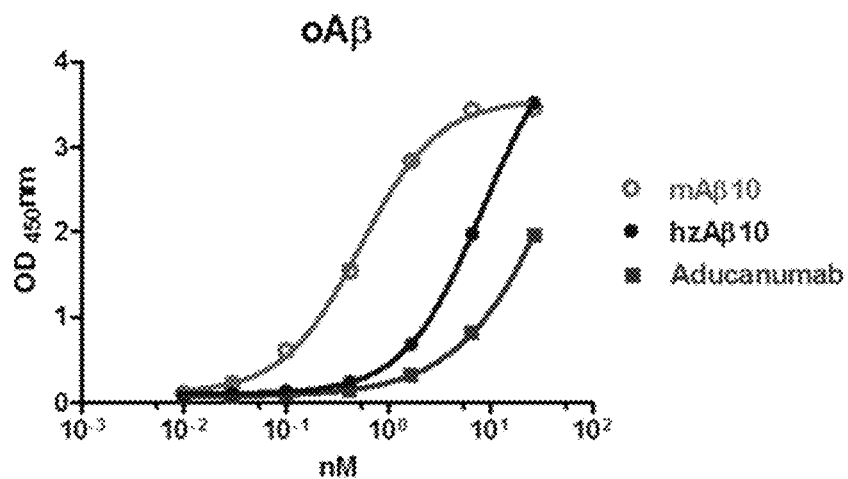

C.

FIG. 8 (Continued)
D.
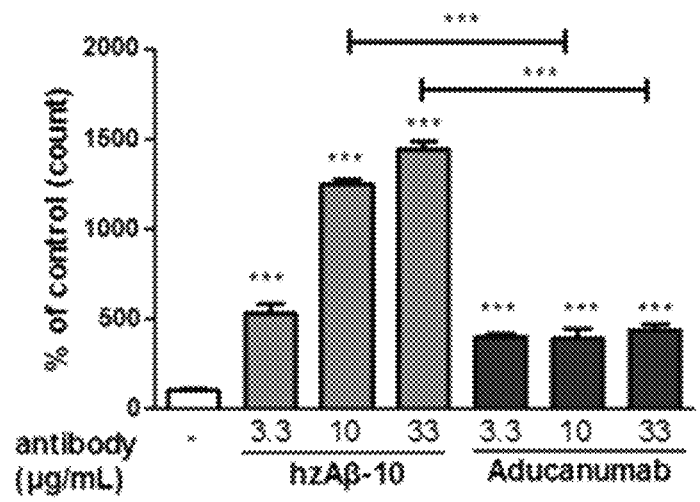
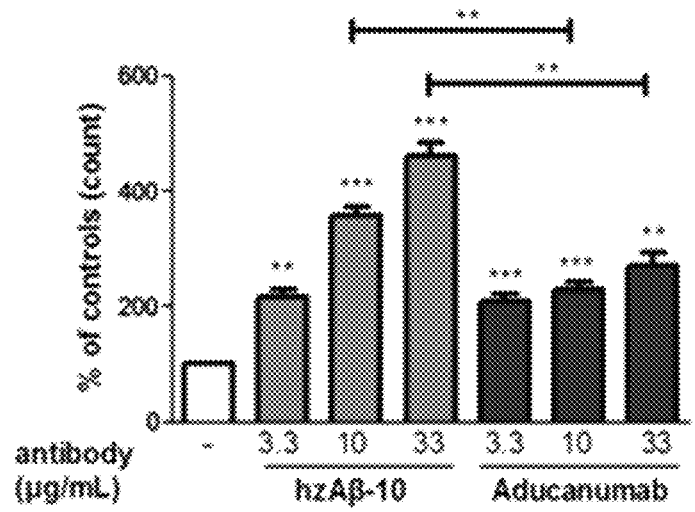

US 11,084,873 B2

ANTI-ABETA ANTIBODIES AND USES THEREOF

CROSS REFERENCE TO RELATED APPLICATION

This application claims priority to U.S. Provisional Application No. 62/678,080, filed on May 30, 2018, the entire content of which is hereby incorporated by reference herein.

BACKGROUND

Alzheimer's Disease (AD) is characterized clinically by progressive memory loss and cognitive dysfunction. Extracellular senile amyloid plaques constituted predominantly of Aβ are some of its pathological hallmarks. See, e.g., Wang et al., Nat Rev Neurol. 2017, 13(10):612-623. The majority of AD cases are sporadic and the etiology of AD remains largely unclear due to its multiplicity of disease origin. Current treatments targeting temporary symptomatic relief do not cure the disease.

In AD, Aβ deposits in the brain instigate pro-inflammatory modes of glial activation and the uncontrolled accumulation of Aβ exacerbates the consequential neuro-inflammation and promotes Tau hyper-phosphorylation, leading to neuronal loss. To date, there is no cure for this devastating disease. Among many disease-modifying approaches, passive immunotherapy using antibody against Aβ is a promising approach to prevent or delay the pathogenesis of AD. See, e.g., Barrera-Ocampo A and Lopera F. Colomb Med (Cali). 2016 Dec. 30; 47(4):203-212; US 2009/0142270A1; and US 2015/0315267A1. The beneficial effects are believed to be attributed to the antibody's effects on alleviating Aβ accumulation via promoting microglial phagocytosis toward Aβ. However, many clinical trials of immunotherapy failed to validate the therapeutic benefits largely due to the lack of improved Aβ clearance and/or the occurrence of the severe adverse effects.

As mentioned above, microglia are thought to play an important role in the pathogenesis of AD, where they become activated and are characterized by morphological changes and by productions of various effectors; some combination of which can be beneficial or detrimental for brain functioning. There is growing consensus that a favorable combination of diminished microglia-mediated neuro-inflammation and enhanced Aβ clearance may be critical in AD therapy. Any means that possess anti-inflammatory properties, while promoting microglial phagocytic activity and neuronal functionality, should be beneficial for treating the diseases. Many strategies for prevention and treatment of AD have aimed to prevent amyloid accumulation or to enhance its clearance. Indeed, systematic delivery of an Aβ monoclonal antibody, 3D6, was shown to have therapeutic efficacy in transgenic mouse models. See, e.g., Bacskai B J et al., J Neurosci. 2002 Sep. 15; 22(18):7873-8. Although the humanized version of this antibody, bapineuzumab, in clinical trials did show lower Aβ burden in the brain by amyloid PET imaging, the clinical trials failed due to no significant clinical benefits and the occurrence of severe adverse effects. Furthermore, subtle but significant neuro-inflammation might appear in the brain many years before the clinical manifestations of AD become detectable. The chronic and self-propelling neuro-inflammation has severely compromised the brain functioning by then, which makes AD treatment more difficult. Thus, intervention at the early stage of the disease with multi-functional effects is emerging as a promising therapeutic paradigm. However, an early diagnosis of AD at preclinical stages and an effective treatment for AD are not available.

To fulfill the unmet needs in AD therapy, novel antibodies are needed that possess multifaceted functionality for attenuating the AD-like pathology, e.g., enhancing Aβ clearance in vitro and in vivo, and promoting neuronal functioning in animals.

SUMMARY

In one aspect, described herein is an isolated antibody. The antibody contains a light-chain CDR1 (L-CDR1) having the sequence of SEQ ID NO: 1, SEQ ID NO: 7, or SEQ ID NO: 14; a light-chain CDR2 (L-CDR2) having the sequence of SEQ ID NO: 2 or SEQ ID NO: 15; a light-chain CDR3 (L-CDR3) having the sequence of SEQ ID NO: 3, SEQ ID NO: 8, SEQ ID NO: 21, or SEQ ID NO: 24; a heavy-chain CDR1 (H-CDR1) having the sequence of SEQ ID NO: 4, SEQ ID NO: 9, SEQ ID NO: 11, SEQ ID NO: 16, or SEQ ID NO: 25; a heavy-chain CDR2 (H-CDR2) having the sequence of SEQ ID NO: 5, SEQ ID NO: 12, SEQ ID NO: 17, SEQ ID NO: 19, SEQ ID NO: 22, or SEQ ID NO: 26; and a heavy-chain CDR3 (H-CDR3) having the sequence of SEQ ID NO: 6, SEQ ID NO: 10, SEQ ID NO: 13, SEQ ID NO: 18, SEQ ID NO: 20, SEQ ID NO: 23, or SEQ ID NO: 27, wherein the antibody specifically binds to $Aβ_{1-42}$ or an N-terminal modified form thereof. In some embodiments, the N-terminal modified $Aβ_{1-42}$ is pyro-glutamate Aβ (pE-Aβ3-42). The antibody can containing an Fc region, an Fab fragment, an Fab' fragment, an F(ab')2 fragment, a single-chain antibody, an scFV multimer, a monoclonal antibody, a monovalent antibody, a multispecific antibody, a humanized antibody, or a chimeric antibody.

In some embodiments, the H-CDR1 has the sequence of SEQ ID NO: 16, the H-CDR2 has the sequence of SEQ ID NO: 19, the H-CDR3 has the sequence of SEQ ID NO: 20, the L-CDR1 has the sequence of SEQ ID NO: 14, the L-CDR2 has the sequence of SEQ ID NO: 15, and the L-CDR3 has the sequence of SEQ ID NO: 3.

In some embodiments, the H-CDR1 has the sequence of SEQ ID NO: 4, the H-CDR2 has the sequence of SEQ ID NO: 5, the H-CDR3 has the sequence of SEQ ID NO: 6, the L-CDR1 has the sequence of SEQ ID NO: 1, the L-CDR2 has the sequence of SEQ ID NO: 2, and the L-CDR3 has the sequence of SEQ ID NO: 3.

In some embodiments, the H-CDR1 has the sequence of SEQ ID NO: 9, the H-CDR2 has the sequence of SEQ ID NO: 5, the H-CDR3 has the sequence of SEQ ID NO: 10, the L-CDR1 has the sequence of SEQ ID NO: 7, the L-CDR2 has the sequence of SEQ ID NO: 2, and the L-CDR3 has the sequence of SEQ ID NO: 8.

In some embodiments, the H-CDR1 has the sequence of SEQ ID NO: 11, the H-CDR2 has the sequence of SEQ ID NO: 12, the H-CDR3 has the sequence of SEQ ID NO: 13, the L-CDR1 has the sequence of SEQ ID NO: 7, the L-CDR2 has the sequence of SEQ ID NO: 2, and the L-CDR3 has the sequence of SEQ ID NO: 3.

In some embodiments, the H-CDR1 has the sequence of SEQ ID NO: 16, the H-CDR2 has the sequence of SEQ ID NO: 17, the H-CDR3 has the sequence of SEQ ID NO: 18, the L-CDR1 has the sequence of SEQ ID NO: 14, the L-CDR2 has the sequence of SEQ ID NO: 15, and the L-CDR3 has the sequence of SEQ ID NO: 3.

In some embodiments, the H-CDR1 has the sequence of SEQ ID NO: 9, the H-CDR2 has the sequence of SEQ ID NO: 22, the H-CDR3 has the sequence of SEQ ID NO: 23, the L-CDR1 has the sequence of SEQ ID NO: 7, the L-CDR2 has the sequence of SEQ ID NO: 2, and the L-CDR3 has the sequence of SEQ ID NO: 21.

In some embodiments, the H-CDR1 has the sequence of SEQ ID NO: 25, the H-CDR2 has the sequence of SEQ ID NO: 26, the H-CDR3 has the sequence of SEQ ID NO: 27, the L-CDR1 has the sequence of SEQ ID NO: 7, the L-CDR2 has the sequence of SEQ ID NO: 2, and the L-CDR3 has the sequence of SEQ ID NO: 24.

In another aspect, provided herein is a pharmaceutical composition that contains any of the antibodies described herein and a pharmaceutically acceptable carrier.

In yet another aspect, described herein is a nucleic acid construct that encodes any of the antibodies described herein or a component thereof.

In one aspect, described herein is a recombinant cell comprising the nucleic acid construct.

In another aspect, contemplated herein is a method for treating Alzheimer's disease in a subject, the method including identifying a subject suffering from Alzheimer's disease and administering to the subject an effective amount of any of the antibodies described herein.

In some embodiments, the identifying step includes administering to the subject any of the antibodies described herein, and measuring a peripheral blood level of Aβ protein in the subject, wherein the peripheral blood level positively correlates with the level of cerebral Aβ protein.

In yet another aspect, described herein is a method for detecting cerebral Aβ protein in a subject, the method including administering to the subject any of the antibodies described herein, and measuring a peripheral blood level of Aβ protein in the subject, wherein the peripheral blood level positively correlates with the level of cerebral Aβ protein.

In one aspect, described herein is a method for labeling an Aβ plaque in a subject, the method includes labeling any of the antibodies described herein with a detectable label, administering the labeled antibody to a subject, and detecting a location of the label in the subject. In some embodiments, the label is radioactive and the detection is carried out by positron emission tomography.

The details of one or more embodiments are set forth in the accompanying drawing and the description below. Other features, objects, and advantages of the embodiments will be apparent from the description and drawing, and from the claims.

BRIEF DESCRIPTION OF THE DRAWINGS

FIG. 1 shows the properties of antibodies against Aβ from mouse monoclonal hybridoma. Seven different clones of hybridoma secreting antibodies specific for Aβ were generated. ELISA was performed to evaluate the Aβ binding affinity of the antibodies (A). These antibodies shared a similar binding epitope at $A\beta_{N3-10}$ (B), and contained all murine IgG isotypes with seven unique sequence combinations in CDR-H3 (C).

FIG. 2 shows the properties of chimeric antibodies. IgG variable domains of mouse antibodies were constructed into a human IgG1 backbone to generate chimeric antibodies. The binding affinity of the chimeric antibodies was evaluated by surface plasmon resonance (SPR) (A). Microglial Aβ uptake was evaluated and the lead antibody in chimeric version, chAβ10, showed the highest score in Aβ uptake (B).

FIG. 5 shows that [$^{124}$I]mAβ-10 detected cerebral Aβ. Positron Emission Tomography/Computed Tomography analysis showed that mAβ-10 crossed the blood brain barrier and could be a diagnostic probe for Aβ deposition in the brain.

DETAILED DESCRIPTION

Figure 3:
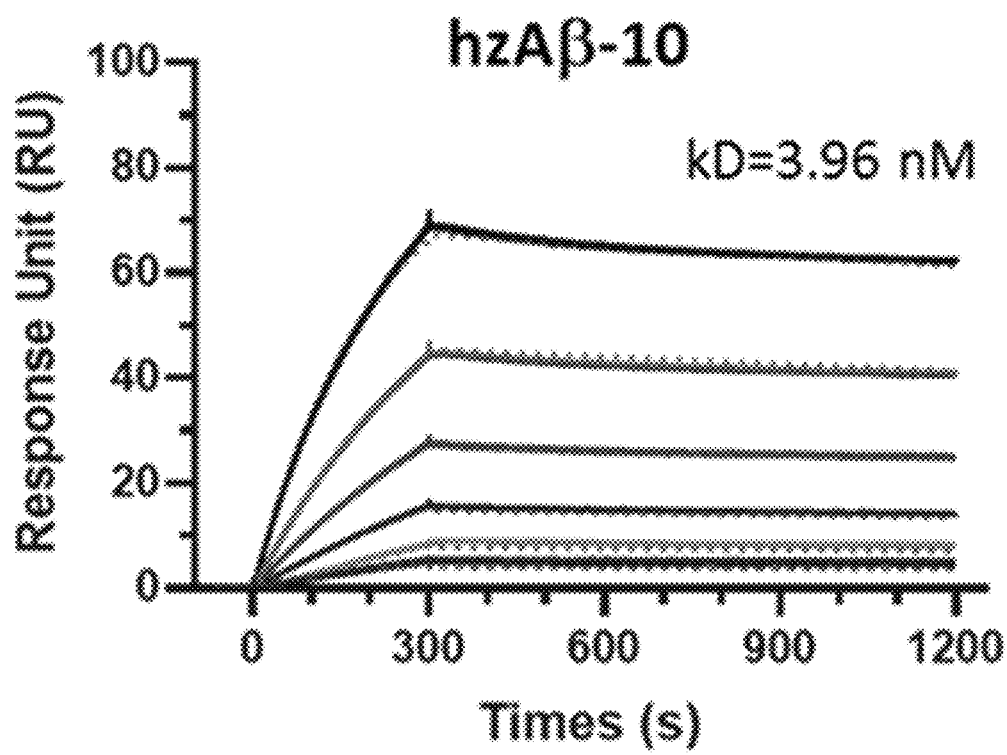
FIG. 3 shows properties of humanized version of the lead antibody: hzAβ-10. Solubility of the lead antibody was examined by FPLC (A). Binding affinity was evaluated by ELISA (B) and SPR (C).

Described herein are novel antibodies that recognize a variety of Aβ species and an N-terminally modified pyro-glutamate Aβ.

The antibodies each include a light-chain CDR1 (L-CDR1) having the sequence of SEQ ID NO: 1, SEQ ID NO: 7, or SEQ ID NO: 14; a light-chain CDR2 (L-CDR2) having the sequence of SEQ ID NO: 2 or SEQ ID NO: 15; a light-chain CDR3 (L-CDR3) having the sequence of SEQ ID NO: 3, SEQ ID NO: 8, SEQ ID NO: 21, or SEQ ID NO: 24; a heavy-chain CDR1 (H-CDR1) having the sequence of SEQ ID NO: 4, SEQ ID NO: 9, SEQ ID NO: 11, SEQ ID NO: 16, or SEQ ID NO: 25; a heavy-chain CDR2 (H-CDR2) having the sequence of SEQ ID NO: 5, SEQ ID NO: 12, SEQ ID NO: 17, SEQ ID NO: 19, SEQ ID NO: 22, or SEQ ID NO: 26; and a heavy-chain CDR3 (H-CDR3) having the sequence of SEQ ID NO: 6, SEQ ID NO: 10, SEQ ID NO: 13, SEQ ID NO: 18, SEQ ID NO: 20, SEQ ID NO: 23, or SEQ ID NO: 27. The antibodies each specifically bind to Aβ1-42 or an N-terminal modified form thereof.

The term "antibody" as used herein includes various antibody structures that have an antigen-binding activity, including but not limited to monoclonal antibodies, polyclonal antibodies, full-length antibodies or fragments thereof, antibodies that contain an Fc region, Fab fragments, Fab' fragments, F(ab')2 fragments, single-chain antibodies, scFV multimers, monovalent antibodies, multivalent antibodies, humanized antibodies, and chimeric antibodies.

Based on the antibody CDR sequences disclosed herein, a skilled practitioner would be able to produce an anti-Aβ antibody in various forms using methods known in the art, e.g., recombinant methods.

Data described below suggest that these antibodies can be used to treat AD and for early detection of cerebral Aβ levels. N-terminally modified pyro-glutamate Aβ (pE-Aβ3-42) is highly prone to aggregation and might be critical for Aβ plaque formation. It was shown that the binding epitopes of these antibodies are mapped to the N-terminus of Aβ peptide specifically recognizing various forms of Aβ species and pE-Aβ3-42. Thus, these antibodies may be more effective in Aβ clearance.

For example, data demonstrated that at least one of the antibodies possesses multifaceted functionality in attenuating the AD-like pathology in APP/PS1 mice and engages Aβ plaques in the brain across the blood-brain barrier, while transforming over-activated microglia into ramified microglia with a healthy and functional morphology. The data further indicated that treatment with the antibody can enhance microglial Aβ phagocytosis and improved neuronal function.

Further, it was shown that intraperitoneal injection of one of the antibodies triggered a robust efflux of cerebral Aβ into the circulation, whereby the increased Aβ levels in the blood were positively correlated with the Aβ levels in the brains of Aβ plaque-loaded or non-Aβ plaque-bearing APP/PS1 mice. In other words, an elevated level of peripheral blood Aβ indicates an elevated cerebral Aβ level. Therefore, measuring the Aβ level in the peripheral blood (e.g., in a serum or plasma sample) induced by the antibody can be used to predict cerebral Aβ level at all disease stages of AD. This innovative approach can serve as a preclinical diagnosis for patients at risk of AD and assist to monitor the status of Aβ pathology in AD patients under intervention. Findings from mechanistic study further revealed that glial rejuvenation and increased astrocytic transthyretin might, at least partly, contribute to the dual efficacy of both treatment and early diagnosis. The studies set out below suggest that the novel antibodies have theranostic potential for AD.

To diagnose AD or determine AD disease stages in a subject, after a subject has been administered one of the antibodies described herein, the peripheral blood Aβ level can be determined. The determined level can be compared to a control level (e.g., a level found in subjects without AD or Aβ plaques) or a level determined in the subject at an earlier time point. Based on the comparison, whether the subject has AD or the severity of AD can be assessed. To monitor the efficacy of an AD treatment in a subject, the peripheral blood Aβ level in the subject can be determined, using the method described herein, before the start of the treatment and at one or more points during the treatment. A decreasing peripheral blood Aβ level indicates that the treatment is effective.

Any of the anti-Aβ antibodies described herein can be formulated as a pharmaceutical composition suitable for various routes of administration, e.g., intravenous, intraarticular, conjunctival, intracranial, intraperitoneal, intrapleural, intramuscular, intrathecal, or subcutaneous route of administration. The pharmaceutical composition can be an aqueous solution or lyophilized formulation. It can contain a pharmaceutically acceptable carrier, e.g., a buffer, excipient, stabilizer, or preservative. The pharmaceutical composition can include other active ingredients that work together with the anti-Aβ antibody, e.g., another therapeutic agent or an adjuvant.

Without further elaboration, it is believed that one skilled in the art can, based on the description above, utilize the present invention to its fullest extent. The specific examples below are to be construed as merely illustrative, and not limitative of the remainder of the disclosure in any way whatsoever. All references cited herein are hereby incorporated by reference in their entirety.

Example 1: Production of Seven Clones of Antibodies Specific for Aβ from Hybridoma To generate hybridoma, oligomeric Aβ (oAβ) was used for mouse immunization. Synthetic $A\beta_{1-42}$ was dissolved in 1,1,1,3,3,3-Hexafluoro-2-propanol (HFIP) followed by evaporation. Dry membrane was re-dissolved in 1×PBS followed by centrifugation to remove fibrillary and aggregated Aβ. The prepared oAβ oligomers were characterized by Western blot using a commercially available Aβ antibody, 6E10. Results showed that the prepared oAβ oligomers constituted a mixture of Aβ species, including monomers, dimers, and various orders of structure of oAβ species with molecular weights ranging from 37 to 250 kDa. The prepared oAβ oligomers were stored at −80° C. until immunization was performed by LTK Biolaboratories for production of monoclonal hybridoma. Antibodies were subjected to analysis for Aβ binding affinity by ELISA (FIG. 1A) and by immunohistochemistry (data not shown). Epitope mapping of the antibodies was performed. See FIG. 1B. Seven different clones of hybridoma that secret antibodies specific for Aβ were generated. Results showed that these antibodies were all IgG isotypes with a similar binding epitope at $A\beta_{N3-10}$. Hybridoma sequencing was carried out to determine the entire CDR sequences of each monoclonal antibody. The isotypes and CDR sequences are shown in FIG. 1C.

Example 2: Generation of Chimeric Antibodies

Mouse IgG variable domains were inserted into a human IgG1 backbone to generate chimeric antibodies. Surface Plasmon Resonance (SPR) by Biacore was performed to evaluate the Aβ binding affinity of 7 chimeric antibodies. See FIG. 2A. Antibody-enhanced microglial Aβ uptake in vitro was performed. Data indicate that all antibodies enhanced microglial Aβ uptake, while the lead antibody appears to have the highest score on the assay. See FIG. 2B.

Example 3: Humanization of mAβ-10

A humanized version of the lead antibody (hzAβ-10) was constructed from chimeric antibody using human IgG1 framework. Fast protein liquid chromatography (FPLC) was used for analysis of protein solubility (FIG. 3A) and characters of Aβ binding were examined by immunofluorescent histochemistry on APP/PS1 mouse brain sections (data not shown), ELISA (FIG. 3B), and SPR (FIG. 3C). Data indicated that hzAβ-10 exhibited an excellent Aβ binding affinity and an exceptional property of very high protein solubility, which is suitable for cell line development.

Example 4: Novel Aβ Antibodies Also Recognize pE-Aβ3-42

Figure 4:
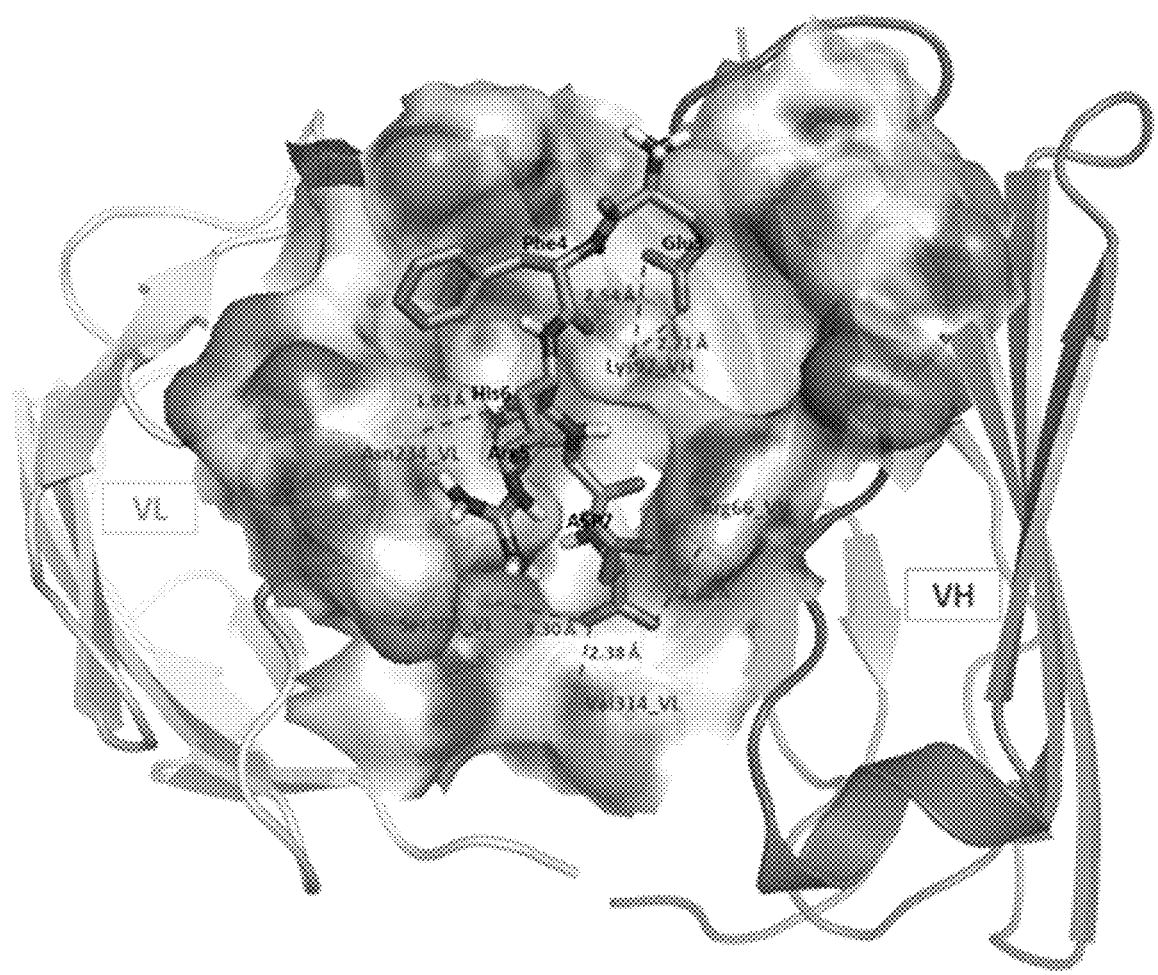
FIG. 4 shows that the lead antibody also recognized pE-A$\beta_{3-42}$. Molecular dynamic modeling predicted binding to pE-A$\beta_{3-42}$ (A), which was confirmed by SPR (B) and by ELISA (C).
Figure 4:
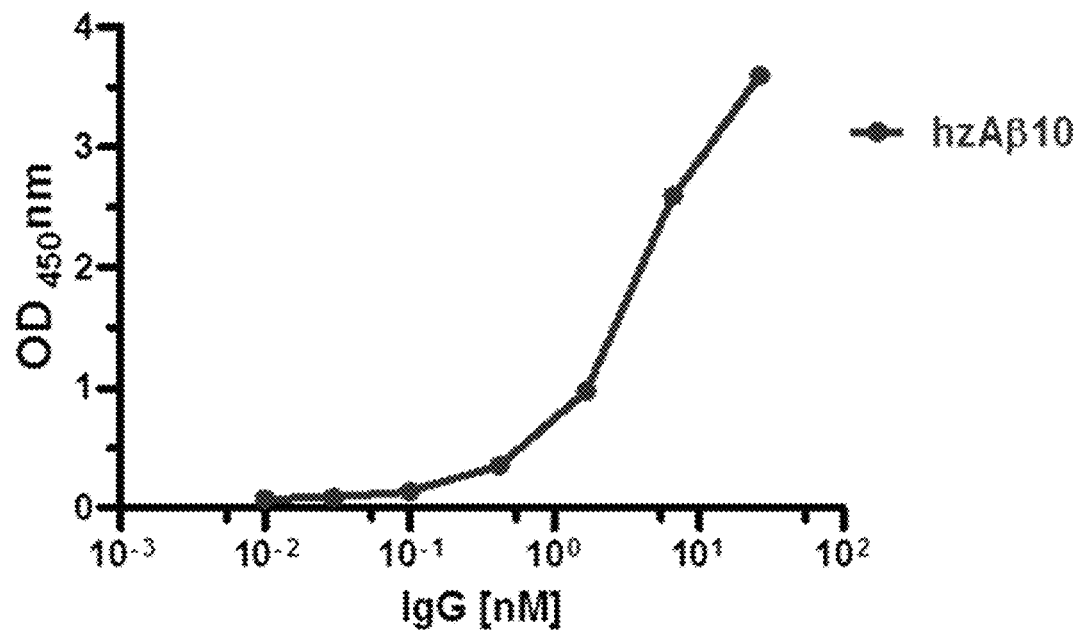

N-terminally modified pyro-glutamate Aβ (pE-$A\beta_{3-42}$) is highly prone to aggregation and might be critical for Aβ plaque formation. The binding epitopes of these antibodies are mapped to N-terminus of Aβ peptide specifically recognizing various forms of Aβ species and pE-$A\beta_{3-42}$ as predicted in the molecular dynamic modeling. See FIG. 4A. Data from Biacore (FIG. 4B) and ELISA (FIG. 4C) confirmed that the lead antibody targeted $A\beta_{1-42}$ and pE-$A\beta_{3-42}$, suggesting that it would be more effective in Aβ clearance.

Example 5: [$^{124}$I]mAβ-10 Detected Cerebral Aβ

APP/PS1 transgenic mice received isotope-labelled antibody ([$^{124}$I]mAβ-10) through i.p. and were subjected to PET/CT analysis. As shown in FIG. 5, results indicated that mAβ-10 crossed the blood-brain barrier and could engage Aβ plaques, suggesting that mAβ-10 could be developed as a diagnostic probe for Aβ deposition in the brain.

Example 6: Early AD Diagnosis by Measuring Antibody-Induced Aβ in the Serum

Figure 6:
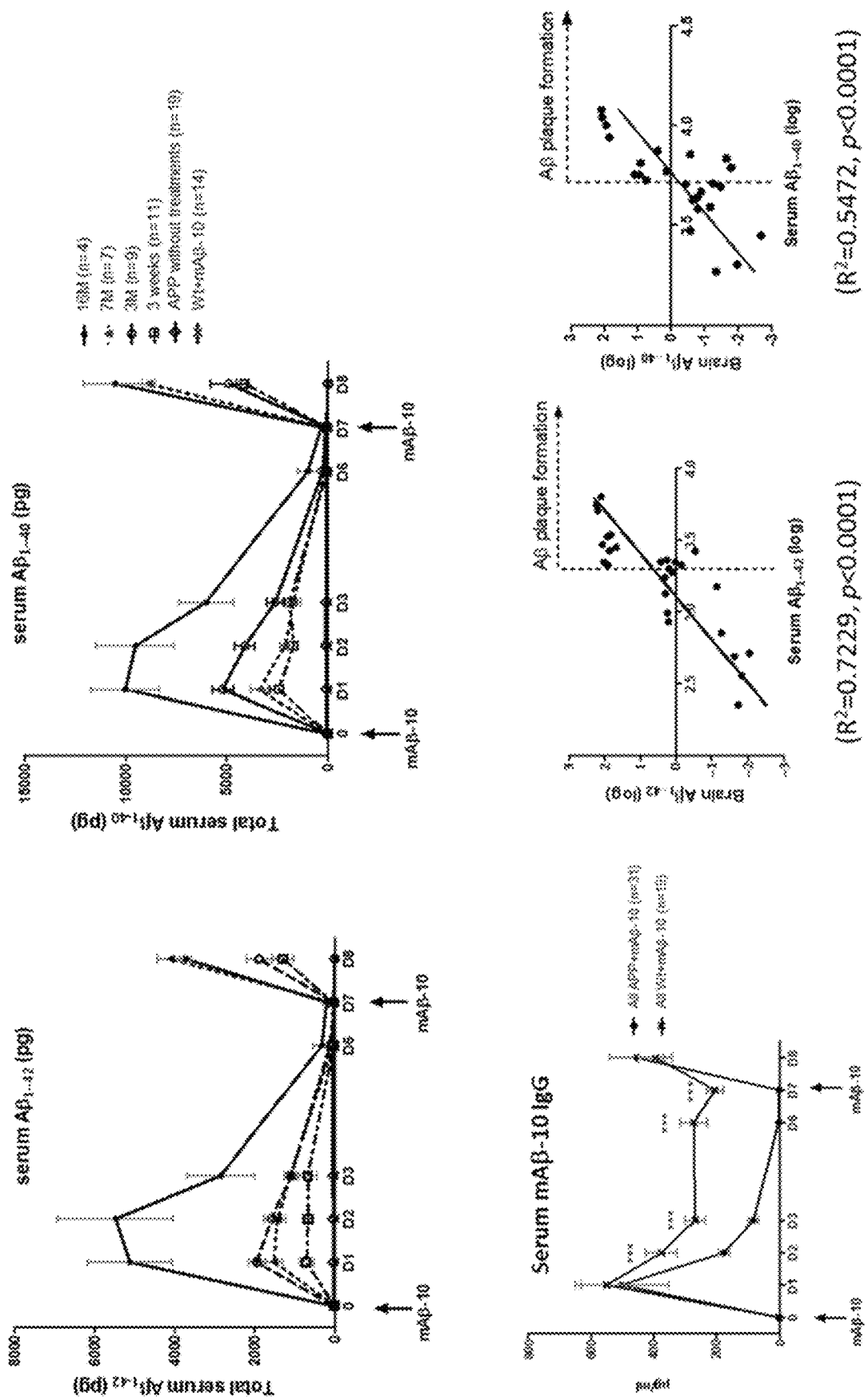
FIG. 6 shows that the lead antibody could be used to predict Aβ levels in the brain by monitoring antibody-induced Aβ in circulation. Intraperitoneal injection of the lead antibody instigated a robust efflux of cerebral Aβ into the blood. The increased Aβ levels in the serum were positively correlated with the cerebral Aβ levels in APP/PS1 mice with or without the presence of Aβ plaques.

A robust transport of cerebral Aβ into the blood was triggered by two doses of mAβ-10 treatments and the escalating serum Aβ levels were highly correlated with the corresponding Aβ levels in Aβ plaques-laden and non-Aβ plaques-bearing APP/PS1 mice. See FIG. 6. Through examining the blood samples, use of this novel antibody could indicate the amount of cerebral Aβ at various stages of the disease and predict the appearance of Aβ plaque formation by evaluating serum Aβ. Furthermore, serum Aβ declined as the circulating antibody descended, suggesting the involvement of the antibody in the clearance of peripheral Aβ. See FIG. 6. This innovative approach might implement the development of early diagnosis for patients at risk of AD or at preclinical stages and aid in monitoring the status of Aβ pathology in AD patients under intervention.

Example 7: Transcriptome Analysis

Figure 7:
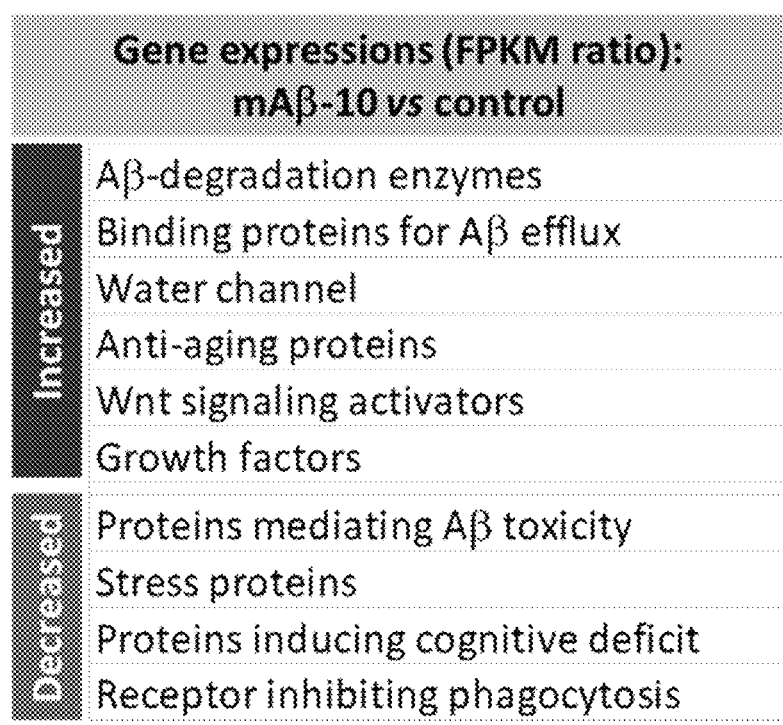
FIG. 7 summarizes NextGen RNA sequencing analysis of gene expressions in the hippocampus from mice injected with mAβ-10. Surprisingly, antibody treatments triggered many genes beneficial against AD, while no indication of neuro-inflammation was found.

NextGen Sequencing RNA-seq analysis, i.e., transcriptome analysis, of the hippocampus was performed to examine the gene expression profile after injection of mAβ-10. Results showed that a total of 47,717 genes showed increased or decreased expression levels. As presented in FIG. 7, many genes with significant upregulation appeared to be beneficial for AD, while genes involved in toxicity and stress were down-regulated.

Example 8: Treatments with hzAβ-10 Rejuvenated Microglia in APP/PS1 Mice

Confocal imaging show that the presence of frustrated microglia without apparent phagocytic activity was observed in aged APP/PS1 mice, while treatment with hzAβ-10 at a dose of 30 mg/kg via i.p. injection for 4 doses (in a period of 17 days) escalated Iba1 immunoreactivity with dramatic changes in morphology resembling functional/ramified microglia (data not shown). These results indicated that treatment of hzAβ-10 rejuvenated microglia and promoted clearance of Aβ plaques in vivo.

Example 9: Treatment with mAβ-10 Increased Astrocytic TTR, Improved Neuronal Functionality, and Reduced Amyloid Plaques in APP/PS1 Mice Confocal images showed that treatments with mAβ-10 at 30 mg/kg via ip injection for two doses increased levels of astrocytic transthyretin (TTR), while low abundance of TTR was observed in astrocytes in age-matched APP/PS1 mice (data not shown). Co-localization data also confirmed the localization of TTR within astrocyte end-feet (data not shown). The results suggested that the antibody-induced-TTR in astrocytes could be involved in the Aβ efflux triggered by mAβ-10. Surprisingly, mAβ-10 also increased immunoreactivity of MAP2 and PSD95 in the hippocampus of APP/PS1, suggesting that mAβ-10 enhanced neuronal functions (data not shown). Further, treatment with mAβ-10 once per week for 39 weeks led to a reduction of amyloid plaques in APP/PS1 mice (data not shown).

Example 10: Comparisons Between Aducanumab and the Lead Antibody

Figure 8:
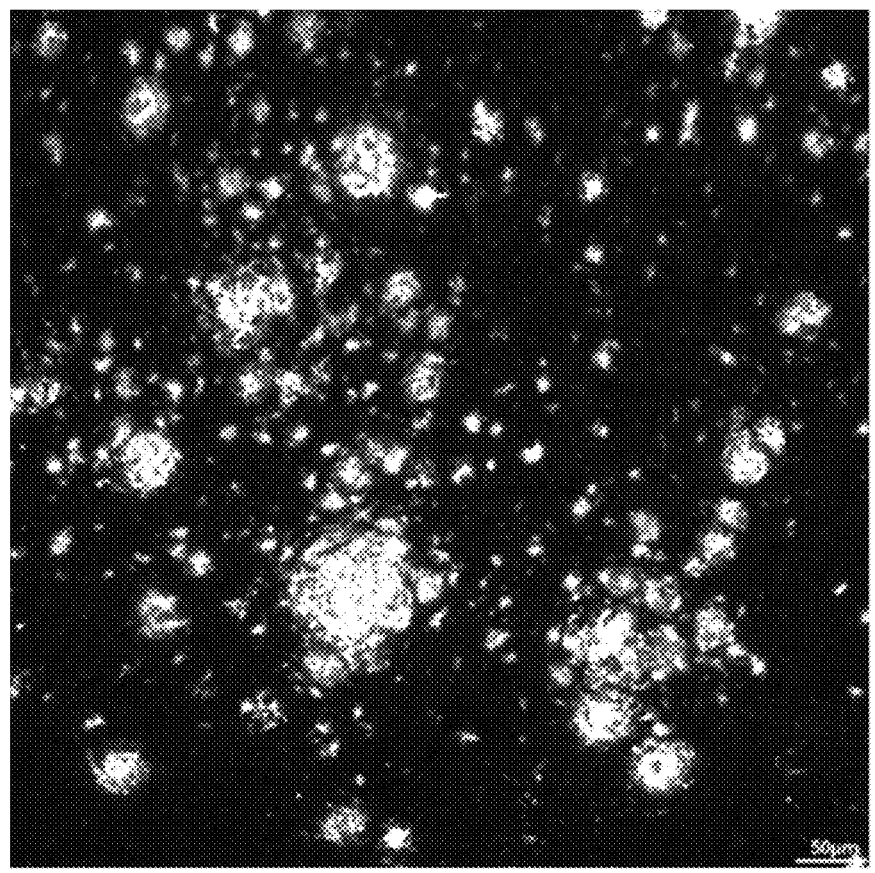
FIG. 8 shows comparisons between Aducanumab and the lead antibody. CDR sequence identity (A), binding affinity to Aβ by ELISA (B), detection of Aβ plaques (C), and microglial Aβ phagocytosis (D) were compared.

Aducanumab (BIIB037 by Biogen) is currently in Phase III clinical trial for AD therapy. The CDR sequences of hzAβ-10 and those of Aducanumab shared very low identity. See FIG. 8A. Compared to Aducanumab (purchased from Creative Biolabs), the lead antibody in either mouse or human versions had stronger affinity for oligomeric Aβ (oAβ) and aggregated Aβ. See FIG. 8B. In contrast to Aducanumab's binding preference to aggregated Aβ, the lead antibody exhibited similar binding affinity for both forms of Aβ. See FIG. 8B. Fluorescent histochemistry followed by confocal Imaging was used to detect Aβ plaques in the brain of APP/PS1 mice at the age of 14 months. See FIG. 8C. Consecutive sections were used for the comparisons between the two antibodies (at 0.2 or 1 mg/ml). Results showed that hzAβ-10 was more sensitive than Aducanumab in detecting cerebral Aβ plaques. Microglial Aβ phagocytosis was evaluated by flow cytometry following the treatments of soluble or aggregated Aβ-FITC for 24 hr. Results showed that hzAβ-10 performed better than Aducanumab in enhancing microglial Aβ phagocytosis. See FIG. 8D.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. An isolated antibody, comprising a light-chain CDR1 (L-CDR1); a light-chain CDR2 (L-CDR2); a light-chain CDR3 (L-CDR3); a heavy-chain CDR1 (H-CDR1); a heavy-chain CDR2 (H-CDR2); and a heavy-chain CDR3 (H-CDR3), wherein the antibody specifically binds to $A\beta_{1-42}$ or an N-terminal modified form of $A\beta_{1-42}$, and wherein:

(i) the H-CDR1 has the sequence of SEQ ID NO: 16, the H-CDR2 has the sequence of SEQ ID NO: 17 or 19, the H-CDR3 has the sequence of SEQ ID NO: 18 or 20, the L-CDR1 has the sequence of SEQ ID NO: 14, the L-CDR2 has the sequence of SEQ ID NO: 15, and the L-CDR3 has the sequence of SEQ ID NO: 3;

(ii) the H-CDR1 has the sequence of SEQ ID NO: 4, the H-CDR2 has the sequence of SEQ ID NO: 5, the H-CDR3 has the sequence of SEQ ID NO: 6, the L-CDR1 has the sequence of SEQ ID NO: 1, the L-CDR2 has the sequence of SEQ ID NO: 2, and the L-CDR3 has the sequence of SEQ ID NO: 3;

(iii) the H-CDR1 has the sequence of SEQ ID NO: 9, the H-CDR2 has the sequence of SEQ ID NO: 5, the H-CDR3 has the sequence of SEQ ID NO: 10, the L-CDR1 has the sequence of SEQ ID NO: 7, the L-CDR2 has the sequence of SEQ ID NO: 2, and the L-CDR3 has the sequence of SEQ ID NO: 8;

(iv) the H-CDR1 has the sequence of SEQ ID NO: 11, the H-CDR2 has the sequence of SEQ ID NO: 12, the H-CDR3 has the sequence of SEQ ID NO: 13, the L-CDR1 has the sequence of SEQ ID NO: 7, the L-CDR2 has the sequence of SEQ ID NO: 2, and the L-CDR3 has the sequence of SEQ ID NO: 3;

(v) the H-CDR1 has the sequence of SEQ ID NO: 9, the H-CDR2 has the sequence of SEQ ID NO: 22, the H-CDR3 has the sequence of SEQ ID NO: 23, the L-CDR1 has the sequence of SEQ ID NO: 7, the L-CDR2 has the sequence of SEQ ID NO: 2, and the L-CDR3 has the sequence of SEQ ID NO: 21; or (vi) the H-CDR1 has the sequence of SEQ ID NO: 25, the H-CDR2 has the sequence of SEQ ID NO: 26, the H-CDR3 has the sequence of SEQ ID NO: 27, the L-CDR1 has the sequence of SEQ ID NO: 7, the L-CDR2 has the sequence of SEQ ID NO: 2, and the L-CDR3 has the sequence of SEQ ID NO: 24.

2. The isolated antibody of claim 1, wherein the H-CDR1 has the sequence of SEQ ID NO: 16, the H-CDR2 has the sequence of SEQ ID NO: 19, the H-CDR3 has the sequence of SEQ ID NO: 20, the L-CDR1 has the sequence of SEQ ID NO: 14, the L-CDR2 has the sequence of SEQ ID NO: 15, and the L-CDR3 has the sequence of SEQ ID NO: 3.

3. The isolated antibody of claim 2, wherein the N-terminal modified $A\beta_{1-42}$ is pyro-glutamate $A\beta$ (pE-$A\beta_{3-42}$).

4. The isolated antibody of claim 1, wherein the N-terminal modified $A\beta_{1-42}$ is pyro-glutamate $A\beta$ (pE-$A\beta_{3-42}$).

5. The isolated antibody of claim 1, wherein the H-CDR1 has the sequence of SEQ ID NO: 4, the H-CDR2 has the sequence of SEQ ID NO: 5, the H-CDR3 has the sequence of SEQ ID NO: 6, the L-CDR1 has the sequence of SEQ ID NO: 1, the L-CDR2 has the sequence of SEQ ID NO: 2, and the L-CDR3 has the sequence of SEQ ID NO: 3.

6. The isolated antibody of claim 1, wherein the H-CDR1 has the sequence of SEQ ID NO: 9, the H-CDR2 has the sequence of SEQ ID NO: 5, the H-CDR3 has the sequence of SEQ ID NO: 10, the L-CDR1 has the sequence of SEQ ID NO: 7, the L-CDR2 has the sequence of SEQ ID NO: 2, and the L-CDR3 has the sequence of SEQ ID NO: 8.

7. The isolated antibody of claim 1, wherein the H-CDR1 has the sequence of SEQ ID NO: 11, the H-CDR2 has the sequence of SEQ ID NO: 12, the H-CDR3 has the sequence of SEQ ID NO: 13, the L-CDR1 has the sequence of SEQ ID NO: 7, the L-CDR2 has the sequence of SEQ ID NO: 2, and the L-CDR3 has the sequence of SEQ ID NO: 3.

8. The isolated antibody of claim 1, wherein the H-CDR1 has the sequence of SEQ ID NO: 16, the H-CDR2 has the sequence of SEQ ID NO: 17, the H-CDR3 has the sequence of SEQ ID NO: 18, the L-CDR1 has the sequence of SEQ ID NO: 14, the L-CDR2 has the sequence of SEQ ID NO: 15, and the L-CDR3 has the sequence of SEQ ID NO: 3.

9. The isolated antibody of claim 1, wherein the H-CDR1 has the sequence of SEQ ID NO: 9, the H-CDR2 has the sequence of SEQ ID NO: 22, the H-CDR3 has the sequence of SEQ ID NO: 23, the L-CDR1 has the sequence of SEQ ID NO: 7, the L-CDR2 has the sequence of SEQ ID NO: 2, and the L-CDR3 has the sequence of SEQ ID NO: 21.

10. The isolated antibody of claim 1, wherein the H-CDR1 has the sequence of SEQ ID NO: 25, the H-CDR2 has the sequence of SEQ ID NO: 26, the H-CDR3 has the sequence of SEQ ID NO: 27, the L-CDR1 has the sequence of SEQ ID NO: 7, the L-CDR2 has the sequence of SEQ ID NO: 2, and the L-CDR3 has the sequence of SEQ ID NO: 24.

11. The antibody of claim 1, wherein the antibody is an antibody containing an Fc region, an Fab fragment, an Fab' fragment, an F(ab')2 fragment, a single-chain antibody, an scFV multimer, a monoclonal antibody, a monovalent antibody, a multispecific antibody, a humanized antibody, or a chimeric antibody.

12. A pharmaceutical composition, comprising the antibody of claim 1 and a pharmaceutically acceptable carrier.

13. The pharmaceutical composition of claim 12, wherein the antibody comprises H-CDR1 having the sequence of SEQ ID NO: 16, H-CDR2 having the sequence of SEQ ID NO: 19, H-CDR3 having the sequence of SEQ ID NO: 20, L-CDR1 having the sequence of SEQ ID NO: 14, L-CDR2 having the sequence of SEQ ID NO: 15, and L-CDR3 having the sequence of SEQ ID NO: 3.

14. A method for treating Alzheimer's disease in a subject, the method comprising identifying a subject suffering from Alzheimer's disease and administering to the subject an effective amount of the antibody of claim 1.

15. The method of claim 14, wherein the antibody comprises H-CDR1 having the sequence of SEQ ID NO: 16, H-CDR2 having the sequence of SEQ ID NO: 19, H-CDR3 having the sequence of SEQ ID NO: 20, L-CDR1 having the sequence of SEQ ID NO: 14, L-CDR2 having the sequence of SEQ ID NO: 15, and L-CDR3 having the sequence of SEQ ID NO: 3.

16. The method of claim 15, wherein the identifying step includes administering to the subject the antibody of claim 1, and measuring a peripheral blood level of AP protein in the subject, wherein the peripheral blood level positively correlates with the level of cerebral AP protein.

17. A method for detecting cerebral AP protein in a subject, the method comprising administering to the subject the antibody of claim 1, and measuring a peripheral blood level of AP protein in the subject, wherein the peripheral blood level positively correlates with the level of cerebral AP protein.

18. The method of claim 17, wherein the antibody comprises H-CDR1 having the sequence of SEQ ID NO: 16, H-CDR2 having the sequence of SEQ ID NO: 19, H-CDR3 having the sequence of SEQ ID NO: 20, L-CDR1 having the sequence of SEQ ID NO: 14, L-CDR2 having the sequence of SEQ ID NO: 15, and L-CDR3 having the sequence of SEQ ID NO: 3.

19. A method for labeling an AP plaque in a subject, the method comprising labeling the antibody of claim 1 with a detectable label, administering the labeled antibody to a subject, and detecting a location of the label in the subject.

20. The method of claim 19, wherein the label is radioactive and the detection is carried out by positron emission tomography.

* * * * *

SEQUENCE LISTING

```
<160> NUMBER OF SEQ ID NOS: 45

<210> SEQ ID NO 1
<211> LENGTH: 17
<212> TYPE: PRT
<213> ORGANISM: Artificial Sequence
<220> FEATURE:
<223> OTHER INFORMATION: CDR-L1

<400> SEQUENCE: 1

Cys Arg Ser Ser Gln Thr Ile Val His Ser Asn Gly Asn Thr Tyr Leu
1               5                   10                  15
```

-continued

Glu

<210> SEQ ID NO 2
<211> LENGTH: 7
<212> TYPE: PRT
<213> ORGANISM: Artificial Sequence
<220> FEATURE:
<223> OTHER INFORMATION: CDR-L2

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: CDR-L3

<400> SEQUENCE: 3

Phe Gln Gly Ser His Val Pro Leu Thr
1               5

<210> SEQ ID NO 4
<211> LENGTH: 7
<212> TYPE: PRT
<213> ORGANISM: Artificial Sequence
<220> FEATURE:
<223> OTHER INFORMATION: CDR-H1

<400> SEQUENCE: 4

Thr Ser Gly Met Asn Val Gly
1               5

<210> SEQ ID NO 5
<211> LENGTH: 16
<212> TYPE: PRT
<213> ORGANISM: Artificial Sequence
<220> FEATURE:
<223> OTHER INFORMATION: CDR-H2

<400> SEQUENCE: 5

His Ile Trp Trp Asp Asp Asp Lys Tyr Tyr Asn Pro Ser Leu Lys Ser
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: mAb I CDR-H3

<400> SEQUENCE: 6

Arg Arg Ser Ile Arg Gly Ser Asp Tyr Phe Asp Tyr
1               5                   10

<210> SEQ ID NO 7
<211> LENGTH: 17
<212> TYPE: PRT
<213> ORGANISM: Artificial Sequence
<220> FEATURE:
<223> OTHER INFORMATION: CDR-L1

<400> SEQUENCE: 7

Cys Arg Ser Ser Gln Ser Ile Val His Ser Asn Gly Asn Thr Tyr Leu

```
1               5                  10                  15

Glu

<210> SEQ ID NO 8
<211> LENGTH: 9
<212> TYPE: PRT
<213> ORGANISM: Artificial Sequence
<220> FEATURE:
<223> OTHER INFORMATION: CDR-L3

<400> SEQUENCE: 8

Phe Gln Gly Ser Leu Val Pro Leu Thr
1               5

<210> SEQ ID NO 9
<211> LENGTH: 7
<212> TYPE: PRT
<213> ORGANISM: Artificial Sequence
<220> FEATURE:
<223> OTHER INFORMATION: CDR-H1

<400> SEQUENCE: 9

Thr Ser Gly Met Gly Val Gly
1               5

<210> SEQ ID NO 10
<211> LENGTH: 14
<212> TYPE: PRT
<213> ORGANISM: Artificial Sequence
<220> FEATURE:
<223> OTHER INFORMATION: mAb II CDR-H3

<400> SEQUENCE: 10

Arg Arg Ala Leu Arg Asn Val Val Ala Asp Ala Met Asp Tyr
1               5                  10

<210> SEQ ID NO 11
<211> LENGTH: 7
<212> TYPE: PRT
<213> ORGANISM: Artificial Sequence
<220> FEATURE:
<223> OTHER INFORMATION: CDR-H1

<400> SEQUENCE: 11

Thr Ser Ala Val Gly Val Ser
1               5

<210> SEQ ID NO 12
<211> LENGTH: 16
<212> TYPE: PRT
<213> ORGANISM: Artificial Sequence
<220> FEATURE:
<223> OTHER INFORMATION: CDR-H2

<400> SEQUENCE: 12

His Ile Tyr Trp Asp Asp Asp Lys Arg Tyr Asn Pro Ser Leu Lys Ser
1               5                  10                  15

<210> SEQ ID NO 13
<211> LENGTH: 14
<212> TYPE: PRT
<213> ORGANISM: Artificial Sequence
<220> FEATURE:
<223> OTHER INFORMATION: mAb III CDR-H3

<400> SEQUENCE: 13
```

```
Arg Arg Pro Tyr Tyr Arg Tyr Asp Val Asp Ala Met Asp Tyr
 1               5                  10
```

<210> SEQ ID NO 14
<211> LENGTH: 17
<212> TYPE: PRT
<213> ORGANISM: Artificial Sequence
<220> FEATURE:
<223> OTHER INFORMATION: CDR-L1

<400> SEQUENCE: 14

```
Cys Arg Ser Ser Gln Asn Ile Val His Ser Asn Gly Asn Thr Tyr Leu
 1               5                  10                  15

Glu
```

<210> SEQ ID NO 15
<211> LENGTH: 7
<212> TYPE: PRT
<213> ORGANISM: Artificial Sequence
<220> FEATURE:
<223> OTHER INFORMATION: CDR-L2

<400> SEQUENCE: 15

```
Thr Val Ser Asn Arg Phe Ser
 1               5
```

<210> SEQ ID NO 16
<211> LENGTH: 7
<212> TYPE: PRT
<213> ORGANISM: Artificial Sequence
<220> FEATURE:
<223> OTHER INFORMATION: CDR-H1

<400> SEQUENCE: 16

```
Ser Ser Val Leu Gly Val Ser
 1               5
```

<210> SEQ ID NO 17
<211> LENGTH: 16
<212> TYPE: PRT
<213> ORGANISM: Artificial Sequence
<220> FEATURE:
<223> OTHER INFORMATION: CDR-H2

<400> SEQUENCE: 17

```
His Ile Tyr Trp Asp Asp Asp Arg Arg Tyr Asn Pro Ser Leu Lys Ser
 1               5                  10                  15
```

<210> SEQ ID NO 18
<211> LENGTH: 14
<212> TYPE: PRT
<213> ORGANISM: Artificial Sequence
<220> FEATURE:
<223> OTHER INFORMATION: mAb IV CDR-H3

<400> SEQUENCE: 18

```
Arg Arg Gly Lys Met Gly Arg Gly Leu Asp Ala Met Asp Tyr
 1               5                  10
```

<210> SEQ ID NO 19
<211> LENGTH: 16
<212> TYPE: PRT
<213> ORGANISM: Artificial Sequence
<220> FEATURE:
<223> OTHER INFORMATION: CDR-H2

<400> SEQUENCE: 19

His Ile Tyr Trp Asp Asp Arg Arg Tyr Asn Pro Ser Leu Arg Ser
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: mAb V CDR-H3

<400> SEQUENCE: 20

Arg Arg Gly Lys Met Gly Arg Gly Leu Asp Ala Leu Asp Phe
1               5                   10

<210> SEQ ID NO 21
<211> LENGTH: 9
<212> TYPE: PRT
<213> ORGANISM: Artificial Sequence
<220> FEATURE:
<223> OTHER INFORMATION: CDR-L3

<400> SEQUENCE: 21

Phe Gln Gly Ser Arg Val Pro Leu Thr
1               5

<210> SEQ ID NO 22
<211> LENGTH: 16
<212> TYPE: PRT
<213> ORGANISM: Artificial Sequence
<220> FEATURE:
<223> OTHER INFORMATION: CDR-H2

<400> SEQUENCE: 22

His Ile Trp Trp Asp Asp Lys Tyr Phe Asn Pro Ser Leu Lys Ser
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: mAb VI CDR-H3

<400> SEQUENCE: 23

Arg Arg Ser Leu Lys Trp Leu Asp Ala Met Asp Tyr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: CDR-L3

<400> SEQUENCE: 24

Phe Gln Ser Ser Arg Val Pro Leu Thr
1               5

<210> SEQ ID NO 25
<211> LENGTH: 7
<212> TYPE: PRT
<213> ORGANISM: Artificial Sequence
<220> FEATURE:
<223> OTHER INFORMATION: CDR-H1

<400> SEQUENCE: 25

```
Thr Ser Gly Met Gly Val Ser
1               5

<210> SEQ ID NO 26
<211> LENGTH: 16
<212> TYPE: PRT
<213> ORGANISM: Artificial Sequence
<220> FEATURE:
<223> OTHER INFORMATION: CDR-H2

<400> SEQUENCE: 26

His Ile Tyr Trp Asp Asp Lys Ser Tyr Asn Pro Ser Leu Lys Ser
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: mAb VII CDR-H3

<400> SEQUENCE: 27

Arg Arg Arg Asn Trp Val Ile Thr Asp Ala Met Glu Tyr
1               5                   10

<210> SEQ ID NO 28
<211> LENGTH: 42
<212> TYPE: PRT
<213> ORGANISM: Artificial Sequence
<220> FEATURE:
<223> OTHER INFORMATION: Abeta 1-42

<400> SEQUENCE: 28

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 29
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 29

Asp Ala Glu Phe Arg His Asp Ser Gly Tyr Gly Ser Gly
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 30
```

Ser Gly Ser Gly Glu Phe Arg His Asp Ser Gly Tyr Glu Val
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 31

Ser Gly Ser Gly Arg His Asp Ser Gly Tyr Glu Val His His
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 32

Ser Gly Ser Gly Asp Ser Gly Tyr Glu Val His His Gln Lys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 33

Ser Gly Ser Gly Gly Tyr Glu Val His His Gln Lys Leu Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 34

Ser Gly Ser Gly Glu Val His His Gln Lys Leu Val Phe Phe
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic polypeptide
<220> FEATURE:

```
<221> NAME/KEY: MISC_FEATURE
<222> LOCATION: (1)..(1)
<223> OTHER INFORMATION: BIOTIN

<400> SEQUENCE: 35

Ser Gly Ser Gly His His Gln Lys Leu Val Phe Phe Ala Glu
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 36

Ser Gly Ser Gly Gln Lys Leu Val Phe Phe Ala Glu Asp Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 37

Ser Gly Ser Gly Leu Val Phe Phe Ala Glu Asp Val Gly Ser
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 38

Ser Gly Ser Gly Phe Phe Ala Glu Asp Val Gly Ser Asn Lys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 39

Ser Gly Ser Gly Ala Glu Asp Val Gly Ser Asn Lys Gly Ala
1               5                   10

<210> SEQ ID NO 40
```

```
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 40

Ser Gly Ser Gly Asp Val Gly Ser Asn Lys Gly Ala Ile Ile Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 41

Ser Gly Ser Gly Gly Ser Asn Lys Gly Ala Ile Ile Gly Leu Met
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 42

Ser Gly Ser Gly Asn Lys Gly Ala Ile Ile Gly Leu Met Val Gly
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 43

Ser Gly Ser Gly Gly Ala Ile Ile Gly Leu Met Val Gly Gly Val
1               5                   10                  15

<210> SEQ ID NO 44
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 44
```

```
Ser Gly Ser Gly Ile Ile Gly Leu Met Val Gly Gly Val Val
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: BIOTIN

<400> SEQUENCE: 45

Ser Gly Ser Gly Gly Leu Met Val Gly Gly Val Val Ile Ala
1               5                   10
```